United States Patent [19]

Inoue et al.

[11] Patent Number: 4,852,574
[45] Date of Patent: Aug. 1, 1989

[54] ELECTROCARDIOGRAM ELECTRODE PAD

[75] Inventors: Hirokatsu Inoue, Chiba; Chuji Shimizu, Funabashi, both of Japan

[73] Assignee: Fukuda Denshi Co., Ltd., Japan

[21] Appl. No.: 296,402

[22] Filed: Jan. 9, 1989

Related U.S. Application Data

[63] Continuation of Ser. No. 132,704, Dec. 11, 1987, abandoned, which is a continuation of Ser. No. 920,527, Oct. 17, 1986, abandoned.

[30] Foreign Application Priority Data

Jun. 6, 1985 [JP] Japan .................................. 60-85418

[51] Int. Cl.⁴ .............................................. A61B 5/04
[52] U.S. Cl. .................................................. 128/643
[58] Field of Search ............................... 128/639–641, 128/643, 644, 798, 802, 803

[56] References Cited

U.S. PATENT DOCUMENTS

| 3,534,733 | 10/1970 | Phipps et al. | 128/643 |
| 4,033,334 | 7/1977 | Fletcher | 128/641 X |
| 4,469,105 | 9/1984 | Staver | 128/643 |

Primary Examiner—Lee S. Cohen
Attorney, Agent, or Firm—Toren, McGeady & Associates

[57] ABSTRACT

An electrocardiogram electrode pad has elasticity and flexibility and encloses an electrocardiogram electrode to be held in close contact with the skin surface of a man to derive a weak current therefrom. The electrocardiogram electrode pad having a bottom wall to be held in contact with the skin surface of the man and a side wall extending from the edge of the bottom wall to be fitted on the electrode section of electrocardiogram electrode. The side wall has a greater thickness for its free end portion than its intermediate and stem portions. The side wall has a pinch portion projecting from the free end to be pinched when fitting and removing the electrocardiogram electrode pad with respect to the electrocardiogram electrode.

6 Claims, 3 Drawing Sheets

ELECTROCARDIOGRAM ELECTRODE PAD

This is a continuation of Ser. No. 132,704 filed Dec. 11, 1987, abandoned, which in turn is a continuation of Ser. No. 920,527, filed Oct. 17, 1986, abandoned.

FIELD OF THE INVENTION

This invention relates to an electrocardiogram electrode pad for covering an electrocardiogram electrode.

PRIOR ART

As is well known in the art, electricity is induced in a man with the activity of the heart, brain, muscles, etc. Particularly, electricity induced in the heart can be detected as a weak current induced on the skin surface of the man by an externally installed electrocardiogram to check for any abnormality of the heart. In the use of the electrocardiogram, its input section is electrically coupled to the living body. To this end, its electrode has to be held in close contact with the surface of the skin.

FIG. 5 shows an electrocardiogram electrode held in close contact with the skin of the surface. The electrocardiogram electrode shown in FIG. 5 adopts a suction method for means for obtaining close contact of the electrode with the skin surface of a man. The electrode 1 is made of rubber and has a semispherical cup-like electrode 2 which serves as an electrode section to detect electromotive force generated in a man in contact with the skin surface 8 thereof. The electrode 1 also has a hollow ball-like rubber member 4. The rubber member 4 has an opening 5, which is communicated by a hollow metal tube 6 with a suction port 3 of the cup-like electrode 2. A terminal 7 is connected to the semispherical outer surface of the cup-like electrode 2 and led to the input side of an electrocardiogram (not shown).

To use the prior art rubber suction electrode 1 having the above construction, the rubber member 4 is first compressed with a hand, then the cup-like electrode 2 is held in contact with the skin surface 8 of a man, and then the urging force of the hand is released. As a result, the pressure in the cup-like electrode is reduced by the elastic restoring force of the rubber member 4, whereby the rubber suction electrode 1 is attached by suction to the skin surface.

With the rubber suction electrode 1 held attached by suction to the skin surface, a weak current that is generated in the heart is led to the electrocardiogram to check for any abnormality of the heart. However, this rubber suction electrode 1 provides a considerable suction force. Therefore, after the rubber suction electrode 1 has been removed, its semicircular trace remains for several days, giving uncomfortability to the patient during this period.

Further, some person may feel ache or inflammation is sometimes produced on the skin. Further, in case of a person who has much hair on the skin surface, the suction property of the electrode is reduced. Further, where the cup-like electrode 2 is held in contact with the skin surface of a man for the measurement of the weak current, accurate measurement of weak current can not be measured due to a contact resistance generated on the skin of the man. To overcome this drawback, it has been in practice to apply cream or the like to the skin surface so as to reduce the contact resistance, the cup-like electrode 2 being held in contact with the applied cream for the measurement of the weak current. However, it is rather cumbersome and inefficient to apply cream every time the measurement of weak current is done.

SUMMARY OF THE INVENTION

The invention has been intended in the light of the above problems in the prior art, and its object is to solve the above problems by fitting an electrode pad on the electrocardiogram electrode.

To attain the above object of the invention, there is provided an electrocardiogram electrode pad having elasticity and flexibility for covering an electrocardiogram electrode to be held in contact with the skin surface of a man to derive a weak current therefrom, the electrocardiogram electrode pad having a bottom wall to be held in contact with the skin surface of the man and a side wall extending from the edge of the bottom wall to be fitted on the electrode section of the electrocardiogram electrode, the side wall having a greater thickness for its free end portion than its intermediate and stem portions, the side wall having a pinch portion projecting from the free end thereof to be pinched when fitting and removing the electrocardiogram electrode pad with respect to the electrocardiogram electrode.

DESCRIPTION OF THE PREFERRED EMBODIMENT

Now, the constitution and functions of the invention will be described with reference to the accompanying drawings.

Figure 1:
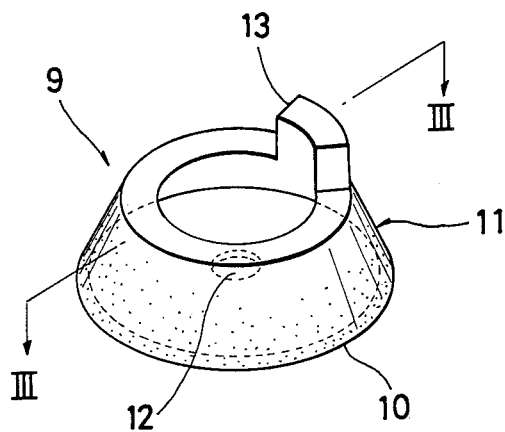
FIG. 1 is a perspective view showing an embodiment of the electrocardiogram electrode pad according to the invention.
Figure 2:
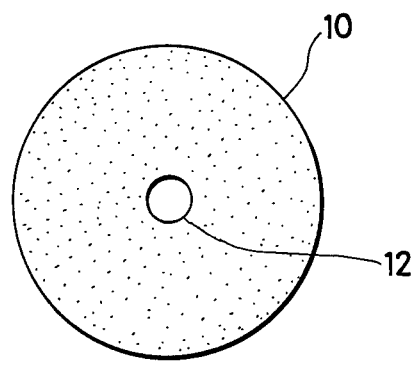
FIG. 2 is a bottom view showing the embodiment of FIG. 1.

FIG. 1 is a perspective view showing an electrocardiogram electrode pad 9 according to the invention. The electrode pad 9 has a substantially cup-like shape. It is made of water-containing gel of a polyurethane resin. Thus, it has high electric conductivity as well as having flexibility and resiliency. The structure of the electrode pad 9 will now be described in detail. Reference numeral 10 designates a bottom wall of the electrode pad 9. The bottom 10 is substantially circular and is in direct contact with the skin surface of a man.

The electrode pad 9 has a side wall 11 integrally extending from the edge of the bottom 10. The side wall 11 is to be fitted on the electrocardiogram electrode and covers the electrode in co-operation with the bottom 10.

Figure 3:
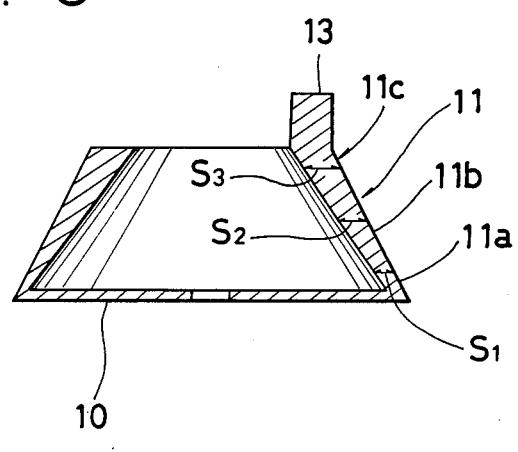
FIG. 3 is a sectional view taken along line III—III in FIG. 1.

The side wall 11, as shown in FIG. 3, is tapered from its stem portion in the neighborhood of the bottom 10 toward its top 11c. Further, the thickness of the side wall 11 increases as one goes toward the top. That is, the thickness s3 of the top portion 11c is greater than the thicknesses s2 and s1 of intermediate and stem portions 11b and 11a. Mathematically, $$s3 > s2 > s1$$

The bottom wall 10 has a substantially central, circular hole 12.

Figure 4:
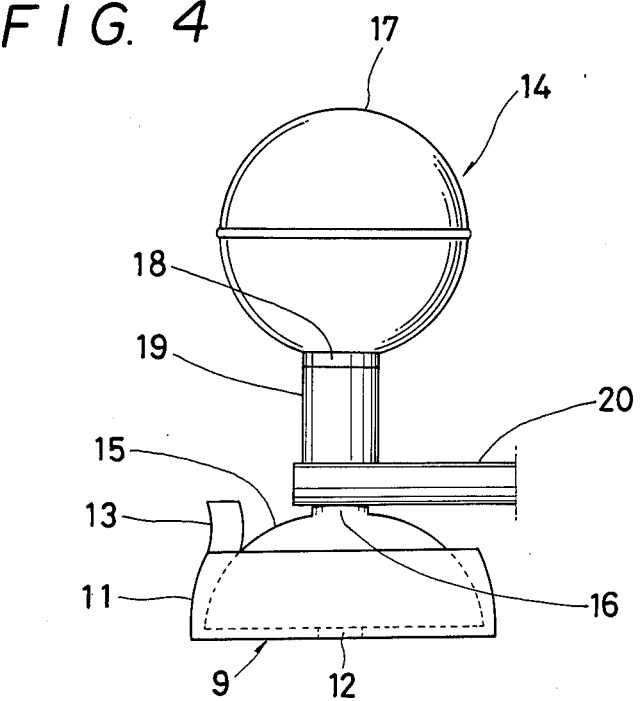
FIG. 4 is a view for explaining the method of use of the electrogram electrode pad.
Figure 5:
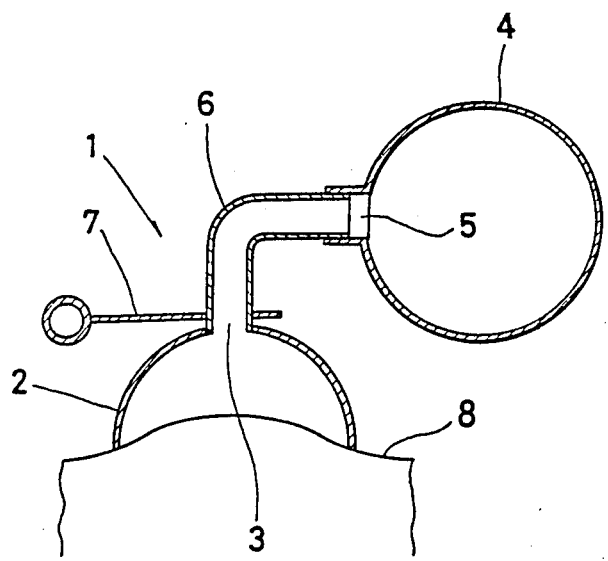
FIG. 5 is a view for explaining the use of a prior art electrocardiogram electrode pad.

Reference numeral 13 designates a pinch portion 13 projecting from the top of the side wall 11. This pinch portion 13 facilitates the fitting of the electrode 14 pad 9 on the electrocardiogram electrode, as shown in FIG. 4, and removing the former from the latter.

In the illustrated embodiment, the pinch portion 13 is integral with and made of the same material as the electrode pad. However, it is possible to form a pinch portion from a different material from the electrode pad, e.g., a woven sheet, a resin sheet or a rubber sheet. The electrode pad 9 is made of water-containing gel and thus has viscosity. Therefore, where the pinch portion is made of the different material noted above from the electrode pad, the electrode pad can be fitted or removed without possibility of attachment of a viscous matter to fingers and thus in a clean and comfortable way by pinching the pinch portion.

Further, the provisions of a pinch portion made from a woven sheet, a resin sheet or a rubber sheet can increase the mechanical strength of the electrode pad 9 which is a soft member. Further, while in this embodiment only a single pinch portion 13 is provided, it is possible to provide two, diametrically opposed pinch portions. Now, the use of the rubber suction pad 9 will be described. FIG. 4 shows the rubber section electrode 14 with the electrode pad 9 fitted thereon. Referring to the Figure, reference numeral 14 designates the rubber suction electrode. The electrode 14 has a construction, in which a suction port 16 of a semi-spherical electrode section for detecting an electromotive force produced in a man and an opening 18 of a hollow ball-like rubber member 17 are communicated with each other by a hollow metal tube 19, to which a terminal 20 led to the input side of an electrocardiogram (not shown) is connected.

The electrode pad 9 is fitted on the rubber suction electrode 14 having the above construction. The electrode pad 9 can be readily fitted by first fitting the side wall 11 on the side opposite the pinch portion 13 on the end of the electrode section 15 of the rubber suction electrode 14, and then pinching and pulling the pinch roller 13 with the thumb and index finger of the right hand while holding the side wall 11 urged against the electrode section 15 by the thumb and index finger of the left hand. In this way, the electrode pad 9 can be readily fitted on the electrode section 15 because it has flexibility.

The fitted electrode pad 9 will not be occasionally detached from the electrode section 15 for the side wall 11 has a greater thickness s3 for its top portion 11c than the intermediate and stem portions 11b and 11a. A satisfactory fit between the electrode section 15 and electrode pad 9 thus can be obtained. Further, since the thickness s3 is greater than the thicknesses s2 and s1, the mechanical stength of the top portion 11c of the side wall 11 can be improved to facilitate the fitting of the pad 9 on the electrode section 15.

The electrode pad 9 can be readily removed from the electrode section 15 of the rubber section electrode 14 by pinching and pulling the pinch portion 13 to the right with the thumb and index finger of the right hand while holding the rubber member 17 with the thumb and index finger of the left hand.

With the electrode pad 9 thus fitted on the rubber section electrode 14, it is held attached by suction to the skin surface of a man for the measurement of a weak current induced in the man. Since the measurement of weak current is done with the electrode pad 9 interposed between the skin surface and electrode section 15 of the rubber suction electrode 14, no trace of the cup-like electrode section will remain on the skin surface.

As has been described in the foregoing, according to the invention an electrode pad is fitted on the electrode section of an electrocardiogram electrode, so that weak current induced in the man is led to the electrode which is held in close contact with the skin surface of the man through the electrode pad, which has electric conductivity. Thus, the weak current in the man can be accurately detached without need of applying any cream to the skin surface.

Further, since the electrode and skin surface are held in close contact via the electrode pad, no trace of the electrode will remain on the skin surface, or there is no possibility of formation of any inflammation even in case of a person having weak skin.

Further, since the side wall of the pad has a greater thickness for its top portion than the intermediate and stem portions, the fitted part will never be occasionally detached from the electrode, and a satisfactory fit between the electrode and pad can be obtained. In consequence, a high quality electrocardiographic waveform can be obtained, and also the reference line of the electrocardiograph can be stabilized to result in less polarization voltage. These properties are desired for the electrocardiographic examination.

Further, since the mechanical strength of the top portion of the side wall 11 of the pad is improved to facilitate the fitting of the pad on the electrode and thus increase the efficiency of the electrocardiographic examination.

Further, the pinch portion facilitates the operation of fitting the electrode pad on the electrode.

Furthermore, since the pinch portion has both flexibility and elasticity, it permits reliable fitting of the pad on the electrode section.

Moreover, since the electrode pad can be handled by pinching the pinch portion and thus without need of touching the bottom of the pad in contact with the skin surface, which is desired from the standpoint of cleanliness. Further, the presence of the pinch portion increases the mechanical strength of the pad.

What is claimed is:

1. An electrocardiogram electrode pad formed of a material having elasticity and flexibility for covering an electrocardiogram electrode to be held in close contact with the skin surface of a man to derive a weak current therefrom, said electrocardiogram electrode pad is electrically conductive and is cup shaped with a hollow interior and a bottom wall to be held in contact with the skin surface of the man, said bottom wall has a circumferentially extending outer edge and a substantially central circular hole therethrough communicating with the hollow interior, and a circumferentially extending side wall extending outwardly from the outer edge of said bottom wall and arranged to be fitted around the electrocardiogram electrode, said side wall having a circumferentially extending stem portion extending from said outer edge outwardly from said bottom wall, a circumferentially extending intermediate portion extending from said stem portion and a circumferentially extending free end portion extending from said intermediate portion away from said outer edge, said side wall having a greater thickness at said free end portion as compared to said stem portion, a pinch portion attached to and projecting outwardly from a limited circumferentially extending part of said free end portion of said side wall in the direction away from said bottom wall and arranged to be pinched when fitting and removing said electrocardiogram electrode pad with respect to an open-ended cup shaped electrode section of an electrocardiogram electrode.

2. An electrocardiogram electrode pad according to claim 1, wherein said side wall has a radially inner circumferentially extending side wall surface and an outer circumferentially extending side wall surface and said side wall surfaces tapering outwardly from one another in the direction from said stem portion to said free end portion.

3. An electrocardiogram electrode pad according to claim 1, wherein said pinch portion is formed of the same material as said cup-shaped portion of said electrocardiogram electrode pad.

4. An electrocardiogram electrode pad according to claim 1, wherein said pinch portion is formed from a woven sheet different from the material forming said electrode pad.

5. An electrocardiogram electrode pad according to claim 1, wherein said pinch portion is formed from a resin sheet different from the material forming said electrode pad.

6. An electrocardiogram electrode pad according to claim 1, wherein said pinch portion is formed from a rubber sheet different from the material forming said electrode pad.

* * * * *